US012579828B2

(12) United States Patent
Che et al.

(10) Patent No.: US 12,579,828 B2
(45) Date of Patent: Mar. 17, 2026

(54) METHOD AND SYSTEM FOR IDENTIFYING TARGET REGION OF DIGITAL PATHOLOGY SLIDE, DEVICE, AND MEDIUM

(71) Applicants: GUANGZHOU KINGMED CENTER FOR CLINICAL LABORATORY, Guangdong (CN); GUANGZHOU KINGMED DIAGNOSTICS GROUP CO., LTD., Guangdong (CN); GUANGZHOU KINGMED TRANSLATIONAL MEDICINE INSTITUTE CO., LTD., Guangdong (CN)

(72) Inventors: Shuanlong Che, Guangdong (CN); Tingsong Yu, Guangdong (CN); Si Liu, Guangdong (CN); Fang Lu, Guangdong (CN); Kangpei Tao, Guangdong (CN); Xin Li, Guangdong (CN); Pifu Luo, Guangdong (CN); Yinghua Li, Guangdong (CN); Weisong Qiu, Guangdong (CN)

(73) Assignees: GUANGZHOU KINGMED CENTER FOR CLINICAL LABORATORY, Guangdong (CN); GUANGZHOU KINGMED DIAGNOSTICS GROUP CO., LTD., Guangdong (CN); GUANGZHOU KINGMED TRANSLATIONAL MEDICINE INSTITUTE CO., LTD., Guangdong (CN)

( * ) Notice: Subject to any disclaimer, the term of this patent is extended or adjusted under 35 U.S.C. 154(b) by 535 days.

(21) Appl. No.: 18/280,270

(22) PCT Filed: Dec. 21, 2020

(86) PCT No.: PCT/CN2020/137872
§ 371 (c)(1),
(2) Date: Sep. 5, 2023

(87) PCT Pub. No.: WO2022/110396
PCT Pub. Date: Jun. 2, 2022

(65) Prior Publication Data
US 2024/0312229 A1     Sep. 19, 2024

(30) Foreign Application Priority Data
Nov. 30, 2020     (CN) ......................... 202011369917.0

(51) Int. Cl.
*G06V 20/69* (2022.01)
*G06V 30/14* (2022.01)
*G16H 70/60* (2018.01)

(52) U.S. Cl.
CPC .......... *G06V 20/695* (2022.01); *G06V 20/698* (2022.01); *G06V 30/1444* (2022.01); *G16H 70/60* (2018.01); *G06V 2201/03* (2022.01)

(58) Field of Classification Search
CPC .............. G06V 20/695; G06V 20/698; G06V 30/1444; G06V 2201/03; G06V 10/82;
(Continued)

(56) References Cited

U.S. PATENT DOCUMENTS

2020/0193236 A1* 6/2020 Oosake ................ G06V 10/454
2020/0342597 A1* 10/2020 Chukka ................... G06T 7/194
(Continued)

FOREIGN PATENT DOCUMENTS

CN         107358611         11/2017
CN         108664937         10/2018
(Continued)

OTHER PUBLICATIONS

"International Search Report (Form PCT/ISA/210) of PCT/CN2020/137872," mailed on Aug. 26, 2021, with English translation thereof, pp. 1-4.
(Continued)

*Primary Examiner* — Han Hoang
(74) *Attorney, Agent, or Firm* — JCIPRNET

(57) ABSTRACT

A method for identifying a target region of a digital pathology slide, including: obtaining a scanned image of a pathology slide; inputting the scanned image of the pathology slide into a preset deep learning-based identification model;
(Continued)

extracting a contour feature of the scanned image of the pathology slide by using an image contour feature extraction submodel, to obtain a contour image; segmenting the contour image by using an image segmentation submodel to obtain a plurality of sub-contour images; separately performing classification and identification on the plurality of sub-contour images by using an image classification submodel, to obtain a region category corresponding to each sub-contour image; and determining a target region image based on the region category of each sub-contour image. In addition, a system for identifying a target region of a digital pathology slide, a device, and a medium are further proposed.

20 Claims, 6 Drawing Sheets

(58) Field of Classification Search
CPC ........ G06V 10/25; G06V 10/44; G16H 70/60; G06F 18/214; G06T 7/0012; G06T 7/11; G06T 7/62
See application file for complete search history.

(56) References Cited

U.S. PATENT DOCUMENTS

| | | | | |
|---|---|---|---|---|
| 2020/0349697 | A1* | 11/2020 | Gao ..................... | G06N 3/0442 |
| 2021/0216745 | A1* | 7/2021 | Gildenblat ............. | G06V 10/44 |
| 2022/0189142 | A1* | 6/2022 | Wang ................... | G06V 10/454 |

FOREIGN PATENT DOCUMENTS

| | | |
|---|---|---|
| CN | 110322436 | 10/2019 |
| CN | 111798966 | 10/2020 |

OTHER PUBLICATIONS

"Written Opinion of the International Searching Authority (Form PCT/ISA/237) of PCT/ CN2020/137872," mailed on Aug. 26, 2021, pp. 1-4.
"Office Action of China Counterpart Application", issued on Jul. 19, 2023, p. 1-p. 8.

* cited by examiner

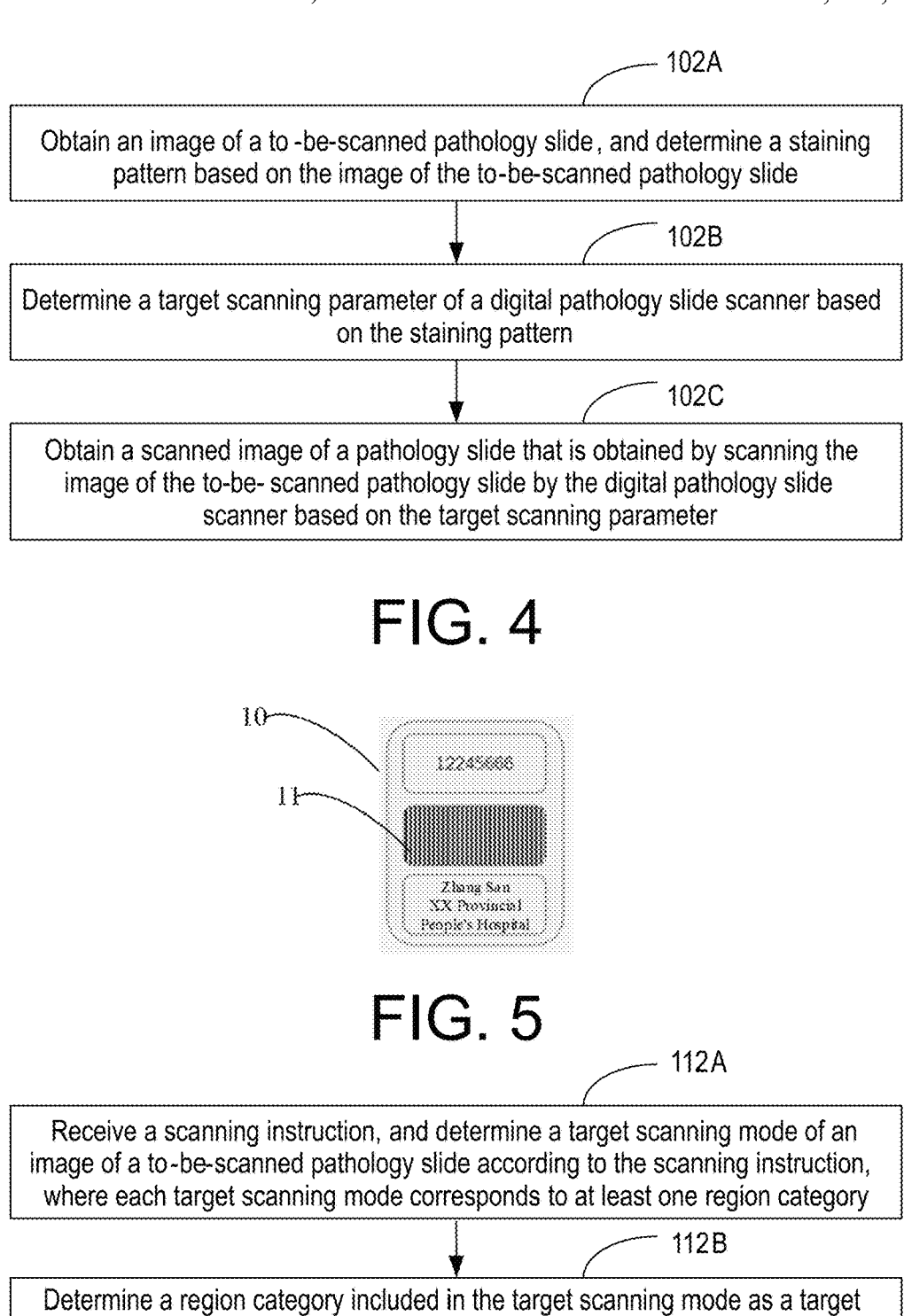

102A

Obtain an image of a to -be-scanned pathology slide, and determine a staining pattern based on the image of the to-be-scanned pathology slide

102B

Determine a target scanning parameter of a digital pathology slide scanner based on the staining pattern

102C

Obtain a scanned image of a pathology slide that is obtained by scanning the image of the to-be- scanned pathology slide by the digital pathology slide scanner based on the target scanning parameter

Receive a scanning instruction, and determine a target scanning mode of an image of a to-be-scanned pathology slide according to the scanning instruction, where each target scanning mode corresponds to at least one region category

112B

Determine a region category included in the target scanning mode as a target region category

112C

Combine the target region category to obtain a target region image

FIG. 6

METHOD AND SYSTEM FOR IDENTIFYING TARGET REGION OF DIGITAL PATHOLOGY SLIDE, DEVICE, AND MEDIUM

CROSS-REFERENCE TO RELATED APPLICATION

This application is a 371 of international application of PCT application serial no. PCT/CN2020/137872, filed on Dec. 21, 2020, which claims the priority benefit of China application no. 202011369917.0, filed on Nov. 30, 2020. The entirety of each of the above-mentioned patent applications is hereby incorporated by reference herein and made a part of this specification.

TECHNICAL FIELD

This application relates to the field of computer technologies, and in particular, to a method and a system for identifying a target region of a digital pathology slide, a device, and a medium.

BACKGROUND ART

Pathological diagnosis refers to observing a pathology slide through a microscope to diagnose a disease. Digital pathology refers to scanning and collecting a high-resolution digital image by using a digital pathology slide scanner, and performing high-precision multi-field seamless splicing and processing to obtain a high-resolution digital pathology slide.

SUMMARY OF THE INVENTION

Technical Problem

However, an existing scanning method for scanning a digital pathology slide by using a scanner has the following disadvantages: 1. Scanning is performed by manually selecting a to-be-scanned region by using naked eyes, which is manpower consuming and material resource consuming. 2. Comprehensive scanning is performed on the digital pathology slide by using a scanner, and consequently many blank regions and unrelated regions are scanned, which reduces working efficiency and scanning quality of the entire scanning process, and large space is occupied by the digital pathology slide.

Technical Solution of the Problem

Technical Solution

Based on this, for the foregoing problem, a method and a system for identifying a target region of a digital pathology slide, a device, and a medium need to be proposed, to improve scanning efficiency and scanning quality of a digital pathology slide.

A method for identifying a target region of a digital pathology slide is provided, and the method includes:

obtaining a scanned image of a pathology slide;

inputting the scanned image of the pathology slide into a preset deep learning-based identification model, where the preset deep learning-based identification model includes an image contour feature extraction submodel, an image segmentation submodel, and an image classification submodel;

extracting a contour feature of the scanned image of the pathology slide by using the image contour feature extraction submodel, to obtain a contour image;

segmenting the contour image by using the image segmentation submodel to obtain a plurality of sub-contour images;

separately performing classification and identification on the plurality of sub-contour images by using the image classification submodel, to obtain a region category corresponding to each of the sub-contour images, where the region category includes one of an effective pathological region, a broken contaminant region, an experimental control region, or a slide information region; and determining a target region image based on the region category of each of the sub-contour images, where the target region image includes an image in at least one region category of the effective pathological region, the broken contaminant region, the experimental control region, and the slide information region.

A system for identifying a target region of a digital pathology slide is provided, and the system includes:

an obtaining module, configured to obtain a scanned image of a pathology slide;

a processing module, configured to input the scanned image of the pathology slide into a preset deep learning-based identification model, where the preset deep learning-based identification model includes an image contour feature extraction submodel, an image segmentation submodel, and an image classification submodel;

an extraction module, configured to extract a contour feature of the scanned image of the pathology slide by using the image contour feature extraction submodel, to obtain a contour image;

a segmentation module, configured to segment the contour image by using the image segmentation submodel to obtain a plurality of sub-contour images;

an identification module, configured to separately perform classification and identification on the plurality of sub-contour images by using the image classification submodel, to obtain a region category corresponding to each of the sub-contour images, where the region category includes one of an effective pathological region, a broken contaminant region, an experimental control region, or a slide information region; and a generation module, configured to determine a target region image based on the region category of each of the sub-contour images, where the target region image includes an image in at least one region category of the effective pathological region, the broken contaminant region, the experimental control region, and the slide information region.

A computer device includes a memory and a processor, the memory stores computer-readable instructions, and when the computer-readable instructions are executed by the processor, the processor is enabled to perform the following steps:

obtaining a scanned image of a pathology slide;

inputting the scanned image of the pathology slide into a preset deep learning-based identification model, where the preset deep learning-based identification model includes an image contour feature extraction submodel, an image segmentation submodel, and an image classification submodel;

extracting a contour feature of the scanned image of the pathology slide by using the image contour feature extraction submodel, to obtain a contour image;

segmenting the contour image by using the image segmentation submodel to obtain a plurality of sub-contour images;

separately performing classification and identification on the plurality of sub-contour images by using the image classification submodel, to obtain a region category corresponding to each of the sub-contour images, where the region category includes one of an effective pathological region, a broken contaminant region, an experimental control region, or a slide information region; and determining a target region image based on the region category of each of the sub-contour images, where the target region image includes an image in at least one region category of the effective pathological region, the broken contaminant region, the experimental control region, and the slide information region.

One or more non-volatile readable storage media storing computer-readable instructions, and when the computer-readable instructions are executed by one or more processors, the one or more processors are enabled to perform the following steps:

obtaining a scanned image of a pathology slide;

inputting the scanned image of the pathology slide into a preset deep learning-based identification model, where the preset deep learning-based identification model includes an image contour feature extraction submodel, an image segmentation submodel, and an image classification submodel;

extracting a contour feature of the scanned image of the pathology slide by using the image contour feature extraction submodel, to obtain a contour image;

segmenting the contour image by using the image segmentation submodel to obtain a plurality of sub-contour images;

separately performing classification and identification on the plurality of sub-contour images by using the image classification submodel, to obtain a region category corresponding to each of the sub-contour images, where the region category includes one of an effective pathological region, a broken contaminant region, an experimental control region, or a slide information region; and determining a target region image based on the region category of each of the sub-contour images, where the target region image includes an image in at least one region category of the effective pathological region, the broken contaminant region, the experimental control region, and the slide information region.

Advantageous Effect of the Invention

Advantageous Effect

The foregoing method and system for identifying a target region of a digital pathology slide, the computer device, and the storage medium include: obtaining a scanned image of a pathology slide; inputting the scanned image of the pathology slide into a preset deep learning-based identification model, where the preset deep learning-based identification model includes an image contour feature extraction submodel, an image segmentation submodel, and an image classification submodel; extracting a contour feature of the scanned image of the pathology slide by using the image contour feature extraction submodel, to obtain a contour image; segmenting the contour image by using the image segmentation submodel to obtain a plurality of sub-contour images; separately performing classification and identification on the plurality of sub-contour images by using the image classification submodel, to obtain a region category corresponding to each of the sub-contour images, where the region category includes one of an effective pathological region, a broken contaminant region, an experimental control region, or a slide information region; and determining a target region image based on the region category of each of the sub-contour images, where the target region image includes an image in at least one region category of the effective pathological region, the broken contaminant region, the experimental control region, and the slide information region. The deep learning-based identification model is used to perform identification and scanning on the scanned image of the pathology slide, improving scanning efficiency and scanning quality of the pathology slide, improving accuracy of the target region image, and reducing memory space of a digital pathology slide.

BRIEF DESCRIPTION OF DRAWINGS

Description of the Drawings

To describe the technical solutions in the embodiments of this application or in the conventional technology more clearly, the following briefly describes the accompanying drawings required for describing the embodiments or the conventional technology. Apparently, the accompanying drawings in the following description show merely some embodiments of this application, and a person of ordinary skill in the art may still derive other drawings from these accompanying drawings without creative efforts.

Figure 1:
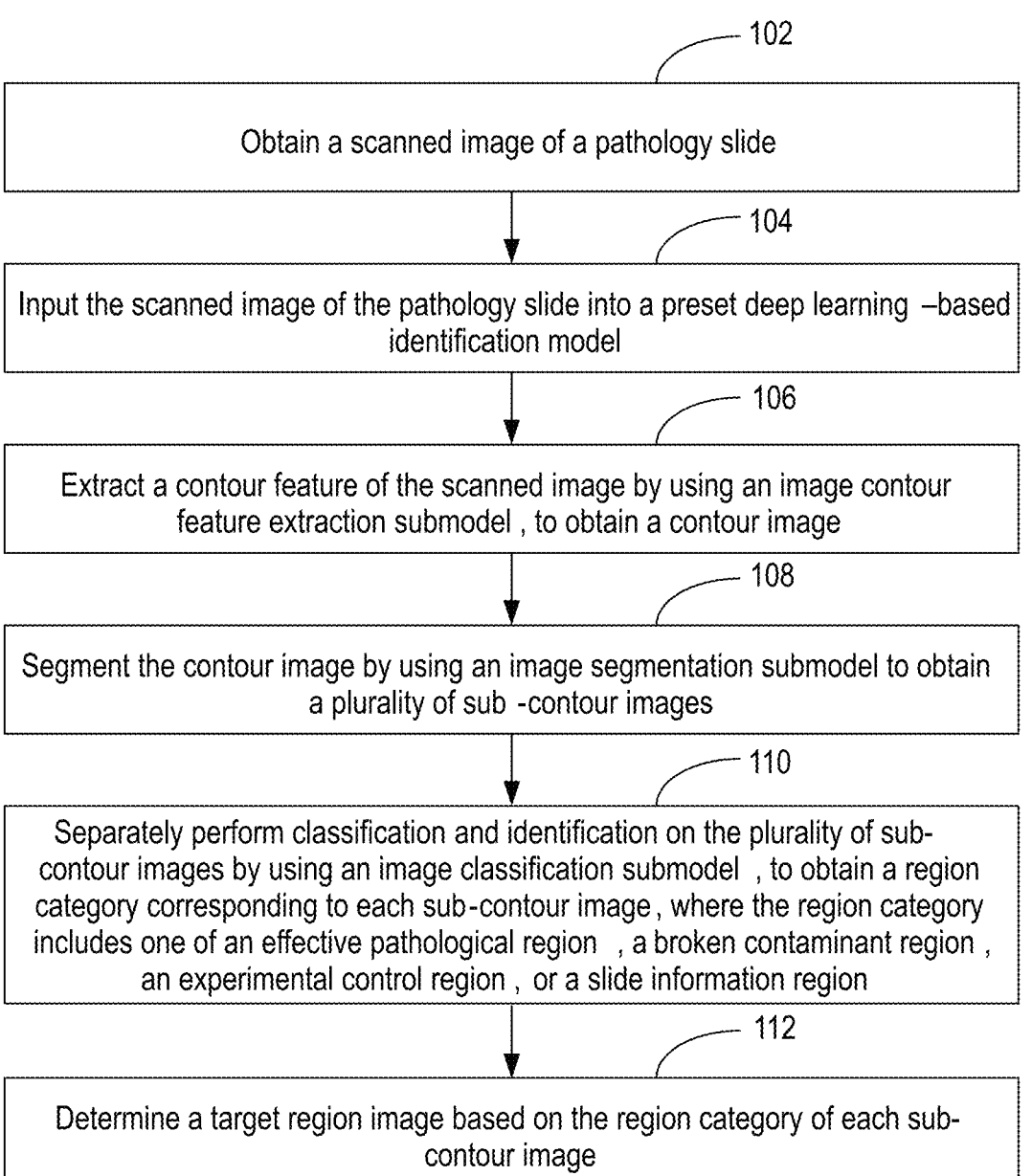
Figure 2:
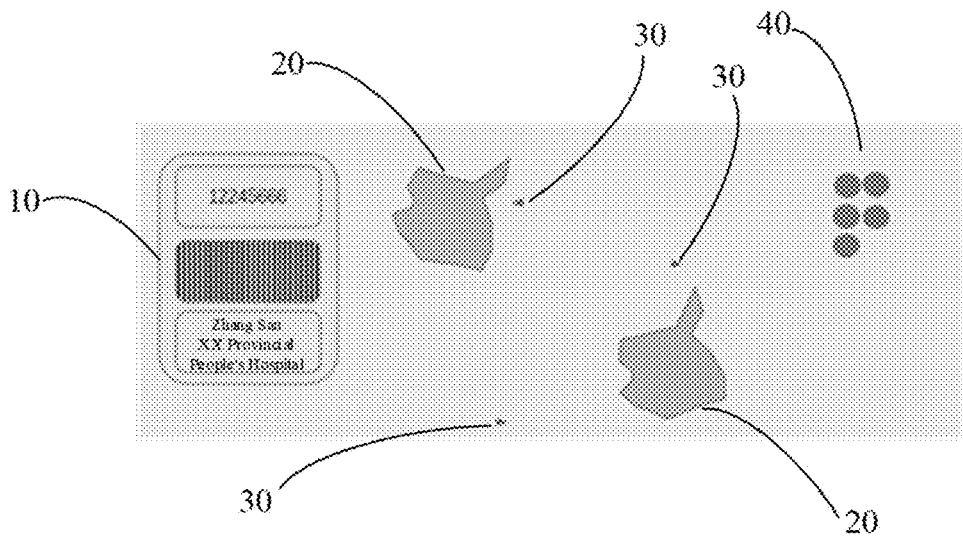
Figure 3A:
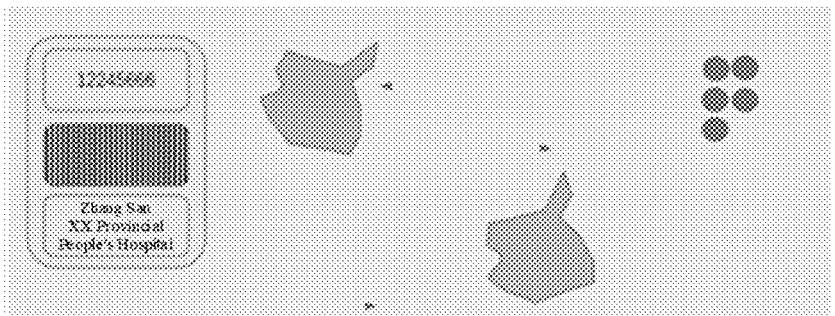
Figure 3B:
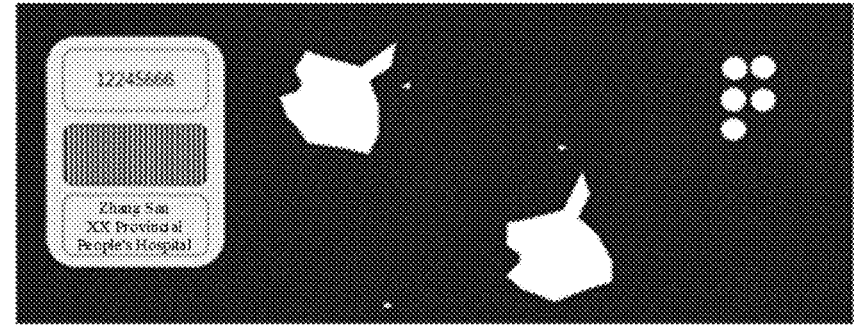
Figure 7:
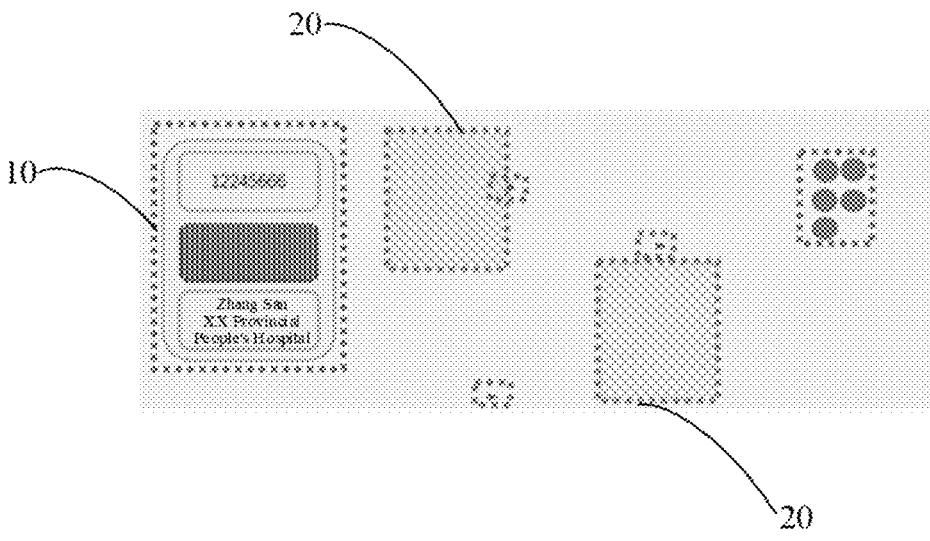
Figure 8:
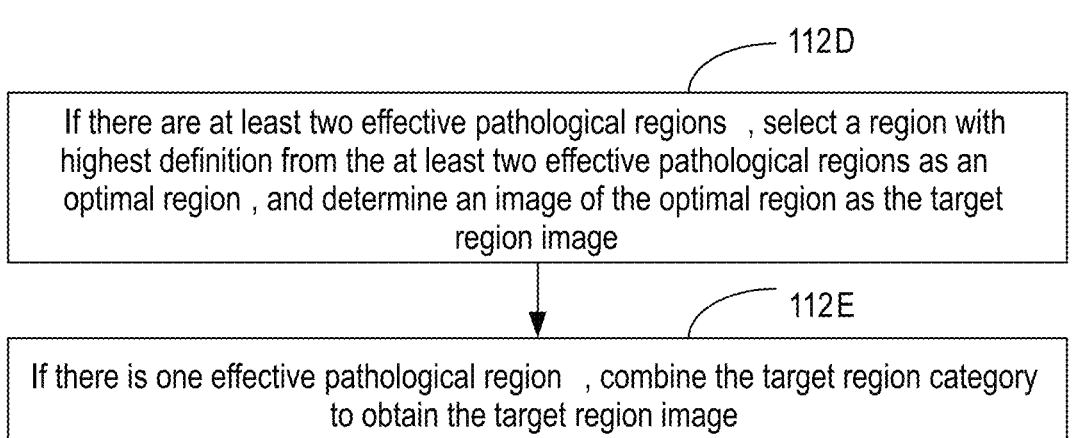
Figure 9:
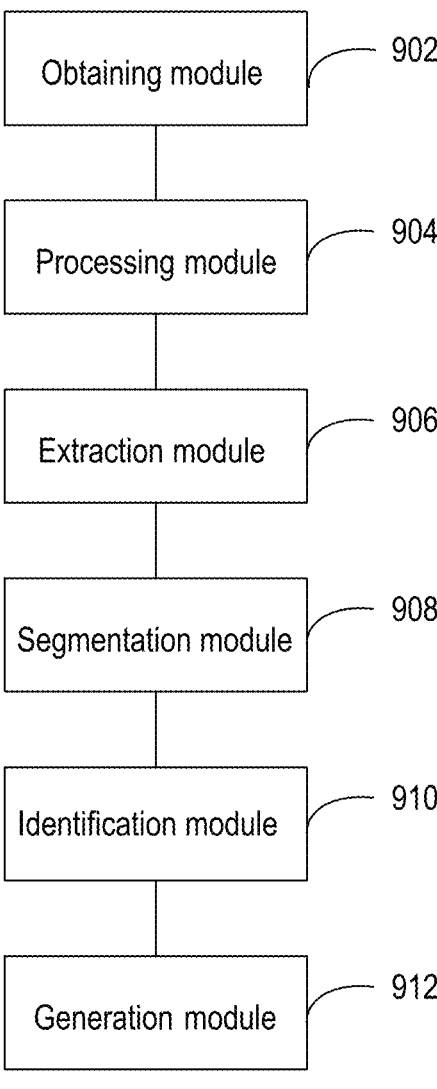
Figure 10:
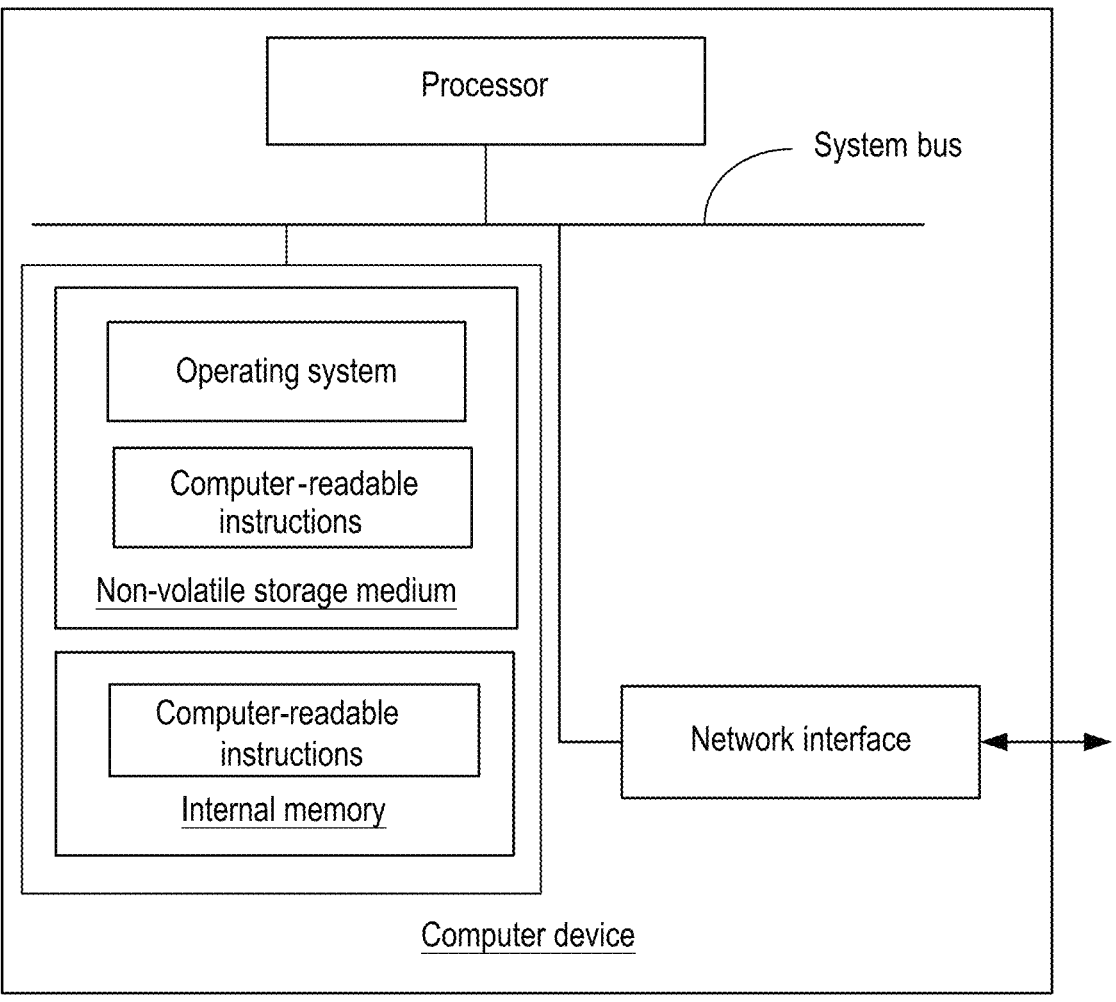

Wherein:

FIG. 1 is a flowchart of a method for identifying a target region of a digital pathology slide according to an embodiment;

FIG. 2 is a schematic diagram of a scanned image of a pathology slide according to an embodiment;

FIG. 3(a) and FIG. 3(b) respectively show a scanned image of a pathology slide and a grayscale binarization image according to an embodiment;

FIG. 4 is a flowchart of a method for generating a scanned image of a pathology slide according to an embodiment;

FIG. 5 is a schematic diagram of information about a to-be-scanned pathology slide according to an embodiment;

FIG. 6 is a schematic diagram of a target region image according to an embodiment;

FIG. 7 is a schematic diagram of a target region image according to another embodiment;

FIG. 8 is a flowchart of a method for generating a target region image according to still another embodiment;

FIG. 9 is a structural block diagram of a system for identifying a target region of a digital pathology slide according to an embodiment; and FIG. 10 is a structural block diagram of a computer device according to an embodiment.

DETAILED DESCRIPTION OF THE EMBODIMENTS

Mode of the Present Invention

The following clearly and completely describes the technical solutions in embodiments of this application with reference to the accompanying drawings in embodiments of this application. Clearly, the described embodiments are merely some rather than all of embodiments of this application. All other embodiments obtained by a person of ordinary skill in the art based on the embodiments of this application without creative efforts shall fall within the protection scope of this application.

As shown in FIG. 1, an embodiment provides a method for identifying a target region of a digital pathology slide. The method for identifying a target region of a digital pathology slide may be applied to both a terminal and a server. This embodiment is described by using an example in which the method is applied to a server. The method for identifying a target region of a digital pathology slide specifically includes the following steps:

Step 102: Obtain a scanned image of a pathology slide.

The scanned image of the pathology slide is a digital image scanned by a digital scanner for the pathology slide. Optionally, the scanned image of the pathology slide may be an image obtained by directly scanning by using a scanner whose scanning parameter is not adjusted, or may be obtained by scanning by using a scanner whose scanning parameter is adjusted for slide information of the pathology slide. As a preference in this embodiment, an image obtained by scanning by using the scanner whose scanning parameter is adjusted for the slide information of the pathology slide is selected as the scanned image of the pathology slide, so that quality of the scanned image of the pathology slide is better, and it is convenient for subsequent efficient identification based on the scanned image of the pathology slide.

Step 104: Input the scanned image of the pathology slide into a preset deep learning-based identification model, where the preset deep learning-based identification model includes an image contour feature extraction submodel, an image segmentation submodel, and an image classification submodel.

Deep learning is used to establish and simulate a neural network of a human brain for analyzing and learning. Deep learning imitates a mechanism of the human brain to interpret data, for example, an image, a sound, and a text, and uses an unsupervised or semi-supervised feature learning and an efficient algorithm based on hierarchical feature extraction to replace manual feature obtaining, which can help improve objectivity and accuracy of a prediction result. The identification model is a deep learning algorithm model that has an identification capability through sample learning. For example, a public deep-learning model training platform, or a structure model such as a CNN (convolutional neural network), Inception V3, or Inception V4 is used to perform identification and classification tasks for a target region image, and establish the deep learning-based identification model. The target region image is an image of an effective region determined by medical personnel for an application scenario of a to-be-scanned pathology slide. For example, for an application scenario of diagnosing a clinical patient inside a laboratory, a target region image corresponding to the application scenario is an image of a region that is of great value for diagnosis and analysis of a disease, namely, an image of an effective pathological region. The preset deep learning-based identification model includes the image contour feature extraction submodel, the image segmentation submodel, and the image classification submodel.

Step 106: Extract a contour feature of the scanned image of the pathology slide by using the image contour feature extraction submodel, to obtain a contour image.

The contour image is used to reflect an image of the contour feature such as a shape and an area of the scanned image of the pathology slide. It may be understood that the scanned image of the pathology slide includes regions in different categories, and contour features of the regions in the categories are different. Therefore, the image contour feature extraction submodel may use a Snake model, an edge algorithm, or the like to extract the contour feature of the scanned image of the pathology slide.

Step 108: Segment the contour image by using the image segmentation submodel to obtain a plurality of sub-contour images.

The image segmentation submodel may segment the contour image by using an FCN (Fully Convolutional Network) network structure, to divide a scanned image of the entire pathology slide into regions to avoid interference of a blank region.

Step 110: Separately perform classification and identification on the plurality of sub-contour images by using the image classification submodel, to obtain a region category corresponding to each of the sub-contour images, where the region category includes one of an effective pathological region, a broken contaminant region, an experimental control region, or a slide information region.

The image classification submodel may be a multi-classification model of naive Bayes, logistic regression, a support vector machine, a random forest, or a long short-term memory LSTM (Long Short-Term Memory) network to perform classification and identification on the plurality of sub-contour images, to obtain the region category corresponding to each sub-contour image. It may be understood that, the image contour feature extraction submodel, the image segmentation submodel, and the image classification submodel are separately obtained through training based on samples of a plurality of digital pathology slides. Therefore, using the deep learning-based identification model to perform segmentation and identification on the scanned image of the pathology slide improves accuracy and objectivity of sub-contour image identification.

Step 112: Determine the target region image based on the region category of each of the sub-contour images, where the target region image includes an image in at least one region category of the effective pathological region, the broken contaminant region, the experimental control region, and the slide information region.

The target region image includes an image in at least one region category of the effective pathological region, the broken contaminant region, the experimental control region, and the slide information region. The effective pathological region is a region of great value for diagnosis and analysis of a disease, and there is at least one effective pathological region. The broken contaminant region is a relatively broken region with a randomly distributed contaminant scattered in the air or a laboratory environment, and there are 0 or more broken contaminant regions. The experimental control region is a region that is added externally to display reliability of a staining result, and there is one experimental control region. The slide information region is a region in which a medical institution, patient information, and slide information are displayed in a number, a text, a two-dimensional code, a barcode, or the like, and there is one slide information region. For example, in a schematic diagram of a scanned image of a pathology slide shown in FIG. 2, 10 is a slide information region, 20 is an effective pathological region, 30 is a broken contaminant region, and 40 is an experimental control region.

Specifically, first, the scanned image of the pathology slide is segmented by using the deep learning-based identification model, segmentation is performed based on different categories of regions to obtain regions in different categories, and the regions in the categories are identified to obtain region category images. Then, corresponding region category images are selected from the identified region category images based on an application scenario of a to-be-scanned pathology slide and are combined as the target region image. An area of the target region image is a relatively small percentage of an area of the scanned image of the pathology slide. Therefore, memory space of a digital pathology slide is reduced. For example, memory of the scanned image is 1 G, and an area percentage of the target region image is 15%. In this case, memory of the target region image is 153 M. Therefore, memory space occupied by the target region image is 7 times lower than that of the scanned image of the pathology slide. In addition, the area percentage of the target region image is 15%, and therefore, scanning efficiency of the target region image is increased by approximately 7 times. It may be understood that performing segmentation and identification on the scanned image of the pathology slide can quickly generate the target region image, avoiding interference of an ineffective region image, improving scanning quality and efficiency of the digital pathology slide, and reducing memory space of the digital pathology slide.

It should be noted that before segmentation and identification are performed on the scanned image of the pathology slide, the scanned image of the pathology slide may be converted into a grayscale binarization image, so that segmentation and identification are more efficiently performed based on the grayscale binarization image, improving identification efficiency of the scanned image of the pathology slide. As shown in FIG. 3(a) and FIG. 3(b), there is respectively a scanned image of a pathology slide and a grayscale binarization image. FIG. 3(a) shows a scanned image of a pathology slide. FIG. 3(b) shows a grayscale binarization image.

The foregoing method for identifying a target region of a digital pathology slide includes: obtaining a scanned image of a pathology slide; inputting the scanned image of the pathology slide into a preset deep learning-based identification model, where the preset deep learning-based identification model includes an image contour feature extraction submodel, an image segmentation submodel, and an image classification submodel; extracting a contour feature of the scanned image of the pathology slide by using the image contour feature extraction submodel, to obtain a contour image; segmenting the contour image by using the image segmentation submodel to obtain a plurality of sub-contour images; separately performing classification and identification on the plurality of sub-contour images by using the image classification submodel, to obtain a region category corresponding to each of the sub-contour images, where the region category includes one of an effective pathological region, a broken contaminant region, an experimental control region, or a slide information region; and determining a target region image based on the region category of each of the sub-contour images, where the target region image includes an image in at least one region category of the effective pathological region, the broken contaminant region, the experimental control region, and the slide information region. The deep learning-based identification model is used to perform identification and scanning on the scanned image of the pathology slide, improving scanning efficiency and scanning quality of the pathology slide, improving accuracy of the target region image, and reducing memory space of the digital pathology slide.

As shown in FIG. 4, in an embodiment, the obtaining a scanned image of a pathology slide includes:

Step 102A: Select a to-be-scanned pathology slide, and determine a staining pattern based on slide information of the to-be-scanned pathology slide.

Step 102B: Determine a target scanning parameter of a digital pathology slide scanner based on the staining pattern.

Step 102C: Obtain the scanned image of the pathology slide that is generated by scanning the to-be-scanned pathology slide by the digital pathology slide scanner based on the target scanning parameter.

A pathology slide image is an image that is of an internal tissue of a human body or a part of the human body and that is obtained in a non-invasive manner, such as HE staining, Papanicolaou stain, special staining, immunohistochemistry, or immunofluorescence, or by using an electron microscope. The pathology slide image is used to perform a pathological diagnosis with reference to clinical data, to determine a benign or malignant disease, type grouping, and a degree of malignancy, determine a prognosis, guide clinical treatment, and the like. The to-be-scanned pathology slide is a slide that needs to be digitally scanned by using the digital pathological scanner. To improve scanning efficiency and quality, in this embodiment, the staining pattern is determined by using pathology slide information, so that the scanning parameter of the digital pathology slide scanner is subsequently adjusted based on the staining pattern of the pathology slide, ensuring scanning quality. Specifically, information about the to-be-scanned pathology slide, for example, a medical institution, patient information, and slide information, may be stored in the to-be-scanned pathology slide in a barcode or two-dimensional code manner. FIG. 5 is a schematic diagram of information about a to-be-scanned pathology slide. In the figure, 10 is the information about the to-be-scanned pathology slide, and 11 is a barcode of the slide information. The slide information of a pathology slide corresponding to the to-be-scanned pathology slide is determined by scanning the barcode or a two-dimensional code. For example, the slide information may be one of staining patterns such as HE staining, IHC staining, TCT staining, blood cell staining, or fluorescence staining.

To avoid a problem that scanning quality is poor because a same scanning parameter is set in a conventional scanning method, in this embodiment, a target scanning parameter of the digital pathology slide is automatically adjusted based on the staining pattern, so that corresponding target scanning parameters are set for different staining patterns, thereby ensuring scanning quality. In addition, the target scanning parameter is automatically determined, so that a scanning worker is prevented from manually selecting different parameters and a misoperation is avoided, thereby further ensuring subsequent scanning quality of the to-be-scanned pathology slide. The target scanning parameter of the digital pathology slide scanner is determined based on the staining pattern. For example, when the staining pattern is HE staining, parameters such as photographing light may be automatically adjusted; when the staining pattern is TCT staining, a Papanicolaou stain parameter may be adjusted; or when the staining pattern is blood cell staining, a Weigert-Giemsa stain parameter may be adjusted. Specifically, the digital pathology slide scanner with an adjusted target scanning parameter is used to scan the to-be-scanned pathology slide to obtain the scanned image of the pathology slide. It may be understood that the scanned image of the pathology slide in this embodiment is an image of the entire to-be-scanned pathology slide, and the scanned image of the pathology slide includes the effective pathological region, the broken contaminant region, the experimental control region, the slide information region, a blank region, and the like.

As shown in FIG. 6, in an embodiment, the determining a target region image based on the region category of each sub-contour image includes:

Step 112A: Receive a scanning instruction, and determine a target scanning mode of the to-be-scanned pathology slide according to the scanning instruction, where each target scanning mode corresponds to at least one region category.

Step 112B: Determine a region category included in the target scanning mode as a target region category.

Step 112C: Combine a target region category to obtain the target region image.

The scanning instruction is an instruction sent by a user to the digital pathology slide scanner based on an application scenario of a pathology slide. The scanning instruction includes a target scanning mode, and the target scanning mode is determined based on an application scenario of a pathology slide, for example, a diagnosis mode for a clinical patient inside a laboratory, a common mode used for teaching and developing an AI algorithm model, a consultation mode for a clinical patient outside a laboratory, an optimization mode used for teaching and developing an AI algorithm model, and a manual selection mode. Each target scanning mode corresponds to at least one region category, for example, the diagnosis mode for a clinical patient inside a laboratory corresponds to at least an effective pathological region. The target region category may be determined based on the region category included in the target scanning mode, and finally, the target region category is combined to obtain the target region image. For example, when the target mode is the diagnosis mode for a clinical patient inside a laboratory, in a schematic diagram of a target region image shown in FIG. 7, a corresponding target region category is a combination of a slide information region 10 and an effective pathological region 20, thereby improving scanning quality and efficiency of the target region image.

In an embodiment, the slide information region is a combination of patient information and hospital information of the slide that are in a character type, and a staining pattern of the slide that is in a barcode or two-dimensional code type.

Specifically, the patient information and the hospital information are marked by using character-type data, and the staining pattern is marked by using barcode or two-dimensional code-type data, so that information displayed in the slide information region is more easily identified, thereby helping improving scanning efficiency.

In an embodiment, the method further includes: identifying the slide information region by using an OCR recognition method, to obtain an identification result; and naming, according to a preset rule, a file corresponding to the target region image based on the identification result.

In this embodiment, the patient information and the hospital information in the character type in the slide information region are identified by using the OCR (Optical Character Recognition, optical character recognition) recognition method. After the identification result is obtained, the file corresponding to the target region image is named. For example, an identifier 1 (12245666) and an identifier 2 (Zhang San) in the identification result are used to generate a target symbol (GZ12245666-Zhang San) in batches according to a preset rule, for example, a rule of a target symbol="GZ"+"identifier 1"+"-"+"identifier 2". Batch naming of the target region image is implemented, so that the target region image is subsequently found quickly based on the named target character.

As shown in FIG. 8, in an embodiment, the combining the target region category to obtain the target region image includes:

Step 112D: If there are at least two effective pathological regions, select a region with highest definition from the at least two effective pathological regions as an optimal region, and determine an image of the optimal region as the target region image.

Step 112E: If there is one effective pathological region, combine the target region category to obtain the target region image.

In this embodiment, when there is one effective pathological region, the target region category is combined, no screening is required, and the target region image is directly obtained. When there are a plurality of effective pathological regions, to improve efficiency of processing the target region image, a region with highest definition is selected as an optimal region based on definition of the effective pathological regions, and an image of the optimal region is determined as the target region image. It may be understood that, the image of the region with highest definition is an image with a highest diagnostic value, which facilitates subsequent efficient processing of the target region image. Further, the image of the optimal region is selected, reducing memory space of the target region image, and improving scanning efficiency of generating the target region image.

In an embodiment, the contour feature is at least one of a color feature, a shape feature, or a location feature of the scanned image of the pathology slide.

In this embodiment, the contour feature is at least one of the color feature, the shape feature, or the location feature of the scanned image of the pathology slide. For example, a contour feature of the effective pathological region is an irregular polygon, and there is at least one irregular polygon, which has a large area, greater than 1 $mm^2$, and is located in a center of a glass slide or is centrally distributed around a center of a glass slide. A region area of the broken contaminant region is small, less than 1 $mm^2$. The experimental control region is a regular shape, for example, a circle. Based on learning and training of the contour feature of the scanned image of the pathology slide, fast and accurate identification and classification can be performed on the scanned image of the pathology slide, thereby improving scanning efficiency and quality.

As shown in FIG. 9, an embodiment provides a system for identifying a target region of a digital pathology slide, and the system includes:

an obtaining module 902, configured to obtain a scanned image of a pathology slide;

a processing module 904, configured to input the scanned image of the pathology slide into a preset deep learning-based identification model, where the preset deep learning-based identification model includes an image contour feature extraction submodel, an image segmentation submodel, and an image classification submodel;

an extraction module 906, configured to extract a contour feature of the scanned image of the pathology slide by using the image contour feature extraction submodel, to obtain a contour image;

a segmentation module 908, configured to segment the contour image by using the image segmentation submodel to obtain a plurality of sub-contour images;

an identification module 910, configured to separately perform classification and identification on the plurality of sub-contour images by using the image classification submodel, to obtain a region category corresponding to each of the sub-contour images, where the region category includes one of an effective pathological region, a broken contaminant region, an experimental control region, or a slide information region; and a generation module 912, configured to determine a target region image based on the region category of each of the sub-contour images, where the target region image includes an image in at least one region category of the effective pathological region, the broken contaminant region, the experimental control region, and the slide information region.

In an embodiment, the obtaining module includes:

a pattern determining unit, configured to select a to-be-scanned pathology slide, and determine a staining pattern based on slide information of the to-be-scanned pathology slide;

a parameter setting unit, configured to determine a target scanning parameter of a digital pathology slide scanner based on the staining pattern; and an image generation unit, configured to obtain the scanned image of the pathology slide that is generated by scanning the to-be-scanned pathology slide by the digital pathology slide scanner based on the target scanning parameter.

In an embodiment, the system for identifying a target region of a digital pathology slide further includes:

an identification module, configured to identify the slide information region by using an OCR recognition method, to obtain an identification result; and a naming module, configured to name, according to a preset rule, a file corresponding to the target region image based on the identification result.

In an embodiment, the generation module includes:

a first determining subunit, configured to: if there are at least two effective pathological regions, select a region with highest definition from the at least two effective pathological regions as an optimal region, and determine an image of the optimal region as the target region image; and a second determining subunit, configured to: if there is one effective pathological region, combine a target region category to obtain the target region image.

FIG. 10 is a diagram of an internal structure of a computer device according to an embodiment. The computer device may be specifically a server, and the server includes but is not limited to a high-performance computer and a high-performance computer cluster. As shown in FIG. 10, the computer device includes a processor, a memory, and a network interface that are connected by using a system bus. The memory includes a non-volatile storage medium and an internal memory. The non-volatile storage medium of the computer device stores an operating system, and may further store computer-readable instructions. When the computer-readable instructions are executed by the processor, the processor may be enabled to implement a method for identifying a target region of a digital pathology slide. The internal memory may also store computer-readable instructions. When the computer-readable instructions are executed by the processor, the processor may be enabled to perform the method for identifying a target region of a digital pathology slide. A person skilled in the art may understand that the structure shown in FIG. 10 is merely a block diagram of a partial structure related to the solutions of this application, and does not constitute a limitation on a computer device to which the solutions of this application are applied. A specific computer device may include more or fewer components than those shown in the figure, or combine some components, or have different component arrangements.

In an embodiment, the method for identifying a target region of a digital pathology slide provided in this application may be implemented in a form of computer-readable instructions, and the computer-readable instructions may be run on the computer device shown in FIG. 10. The memory of the computer device may store various program templates constituting a system for identifying a target region of a digital pathology slide, for example, the obtaining module 902, the processing module 904, the extraction module 906, the segmentation module 908, the identification module 910, and the generation module 912.

A computer device includes a memory, a processor, and computer-readable instructions stored in the memory and capable of running on the processor. When executing the computer-readable instructions, the processor implements the following steps: obtaining a scanned image of a pathology slide; inputting the scanned image of the pathology slide into a preset deep learning-based identification model, where the preset deep learning-based identification model includes an image contour feature extraction submodel, an image segmentation submodel, and an image classification submodel; extracting a contour feature of the scanned image of the pathology slide by using the image contour feature extraction submodel, to obtain a contour image; segmenting the contour image by using the image segmentation submodel to obtain a plurality of sub-contour images; separately performing classification and identification on the plurality of sub-contour images by using the image classification submodel, to obtain a region category corresponding to each of the sub-contour images, where the region category includes one of an effective pathological region, a broken contaminant region, an experimental control region, or a slide information region; and determining a target region image based on the region category of each of the sub-contour images, where the target region image includes an image in at least one region category of the effective pathological region, the broken contaminant region, the experimental control region, and the slide information region.

In an embodiment, the obtaining a scanned image of a pathology slide includes: selecting a to-be-scanned pathology slide, and determining a staining pattern based on slide information of the to-be-scanned pathology slide; determining a target scanning parameter of a digital pathology slide scanner based on the staining pattern; and obtaining the scanned image of the pathology slide that is generated by scanning the to-be-scanned pathology slide by the digital pathology slide scanner based on the target scanning parameter.

In an embodiment, the determining a target region image based on the region category of each of the sub-contour images includes: receiving a scanning instruction, and determining a target scanning mode of the to-be-scanned pathology slide according to the scanning instruction, where each target scanning mode corresponds to at least one of the region categories; determining a region category included in the target scanning mode as a target region category; and combining the target region category to obtain the target region image.

In an embodiment, the slide information region is a combination of patient information and hospital information of the slide that are in a character type, and a staining pattern of the slide that is in a barcode or two-dimensional code type.

In an embodiment, the method further includes: identifying the slide information region by using an OCR recognition method, to obtain an identification result; and naming, according to a preset rule, a file corresponding to the target region image based on the identification result.

In an embodiment, the combining the target region category to obtain the target region image includes: if there are at least two effective pathological regions, selecting a region with highest definition from the at least two effective pathological regions as an optimal region, and determining an image of the optimal region as the target region image; or if there is one effective pathological region, combining the target region category to obtain the target region image.

In an embodiment, the contour feature is at least one of a color feature, a shape feature, or a location feature of the scanned image of the pathology slide.

One or more non-volatile readable storage media storing computer-readable instructions, and when the computer-readable instructions are executed by one or more processors, the one or more processors are enabled to perform the following steps: obtaining a scanned image of a pathology slide; inputting the scanned image of the pathology slide into a preset deep learning-based identification model, where the preset deep learning-based identification model includes an image contour feature extraction submodel, an image segmentation submodel, and an image classification submodel; extracting a contour feature of the scanned image of the pathology slide by using the image contour feature extraction submodel, to obtain a contour image; segmenting the contour image by using the image segmentation submodel to obtain a plurality of sub-contour images; separately performing classification and identification on the plurality of sub-contour images by using the image classification submodel, to obtain a region category corresponding to each of the sub-contour images, where the region category includes one of an effective pathological region, a broken contaminant region, an experimental control region, or a slide information region; and determining a target region image based on the region category of each of the sub-contour images, where the target region image includes an image in at least one region category of the effective pathological region, the broken contaminant region, the experimental control region, and the slide information region.

In an embodiment, the obtaining a scanned image of a pathology slide includes: selecting a to-be-scanned pathology slide, and determining a staining pattern based on slide information of the to-be-scanned pathology slide; determining a target scanning parameter of a digital pathology slide scanner based on the staining pattern; and obtaining the scanned image of the pathology slide that is generated by scanning the to-be-scanned pathology slide by the digital pathology slide scanner based on the target scanning parameter.

In an embodiment, the determining a target region image based on the region category of each of the sub-contour images includes: receiving a scanning instruction, and determining a target scanning mode of the to-be-scanned pathology slide according to the scanning instruction, where each target scanning mode corresponds to at least one of the region categories; determining a region category included in the target scanning mode as a target region category; and combining the target region category to obtain the target region image.

In an embodiment, the slide information region is a combination of patient information and hospital information of the slide that are in a character type, and a staining pattern of the slide that is in a barcode or two-dimensional code type.

In an embodiment, the method further includes: identifying the slide information region by using an OCR recognition method, to obtain an identification result; and naming, according to a preset rule, a file corresponding to the target region image based on the identification result.

In an embodiment, the combining the target region category to obtain the target region image includes: if there are at least two effective pathological regions, selecting a region with highest definition from the at least two effective pathological regions as an optimal region, and determining an image of the optimal region as the target region image; or if there is one effective pathological region, combining the target region category to obtain the target region image.

In an embodiment, the contour feature is at least one of a color feature, a shape feature, or a location feature of the scanned image of the pathology slide.

A person of ordinary skill in the art may understand that all or some of the processes in the methods in the foregoing embodiments may be implemented by computer-readable instructions instructing related hardware. The program may be stored in a non-volatile computer-readable storage medium. When the program is executed, the processes in the foregoing method embodiments may be included. Any reference to a memory, a storage, a database, or another medium used in the embodiments provided in this application may include a non-volatile and/or volatile memory. The non-volatile memory may include a read-only memory (ROM), a programmable ROM (PROM), an electrically programmable ROM (EPROM), an electrically erasable programmable ROM (EEPROM), or a flash memory. The volatile memory may include a random access memory (RAM) or an external cache memory. As an illustration and not a limitation, the RAM may be obtained in a plurality of forms, such as static RAM (SRAM), dynamic RAM (DRAM), synchronous DRAM (SDRAM), dual data rate SDRAM (DDRSDRAM), enhanced SDRAM (ESDRAM), synchronous link (Synchlink) DRAM (SLDRAM), Rambus (Rambus) direct RAM (RDRAM), direct Rambus dynamic RAM (DRDRAM), and Rambus dynamic RAM (RDRAM).

The technical features in the foregoing embodiments may be combined randomly. To make the description brief, not all possible combinations of the technical features in the foregoing embodiments are described. However, as long as there is no contradiction between the combinations of the technical features, the combinations of the technical features should be considered to fall within the scope described in this specification.

The foregoing embodiments represent only several implementations of this application, and description thereof is relatively specific and detailed, but may not be construed as a limitation on the scope of this application. It should be noted that a person of ordinary skill in the art may make some modifications and improvements without departing from the concept of this application, which fall within the protection scope of this application. Therefore, the protection scope of this application shall be subject to the appended claims.

What is claimed is:

1. A method for identifying a target region of a digital pathology slide, wherein the method comprising:

obtaining a scanned image of a pathology slide;

inputting the scanned image of the pathology slide into a preset deep learning-based identification model, wherein the preset deep learning-based identification model comprises an image contour feature extraction submodel, an image segmentation submodel, and an image classification submodel;

extracting a contour feature of the scanned image of the pathology slide by using the image contour feature extraction submodel, to obtain a contour image;

segmenting the contour image by using the image segmentation submodel to obtain a plurality of sub-contour images;

separately performing classification and identification on the plurality of sub-contour images by using the image classification submodel, to obtain a region category corresponding to each of the sub-contour images, wherein the region category comprises one of an effective pathological region, wherein effective pathological region is defined as a region in which a diagnosis and analysis of a disease can be determined, a broken contaminant region, a experimental control region, and a slide information region; and determining a target region image based on the region category of each of the sub-contour images, wherein the target region image comprises an image in at least one region category of the effective pathological region, the broken contaminant region, the experimental control region, and the slide information region.

2. The method for identifying a target region of a digital pathology slide according to claim 1, wherein the obtaining a scanned image of a pathology slide comprises:

selecting a to-be-scanned pathology slide, and determining a staining pattern based on slide information of the to-be-scanned pathology slide;

determining a target scanning parameter of a digital pathology slide scanner based on the staining pattern; and obtaining the scanned image of the pathology slide that is generated by scanning the to-be-scanned pathology slide by the digital pathology slide scanner based on the target scanning parameter.

3. The method for identifying a target region of a digital pathology slide according to claim 1, wherein the determining a target region image based on the region category of each of the sub-contour images comprises:

receiving a scanning instruction, and determining a target scanning mode of a to-be-scanned pathology slide according to the scanning instruction, wherein each target scanning mode corresponds to at least one of the region categories;

determining a region category comprised in the target scanning mode as a target region category; and combining the target region category to obtain the target region image.

4. The method for identifying a target region of a digital pathology slide according to claim 3, wherein the combining the target region category to obtain the target region image comprises:

if there are at least two effective pathological regions, selecting a region with highest definition from the at least two effective pathological regions as an optimal region, and determining an image of the optimal region as the target region image; or if there is one effective pathological region, combining the target region category to obtain the target region image.

5. The method for identifying a target region of a digital pathology slide according to claim 1, wherein the slide information region is a combination of patient information and hospital information of the slide that are in a character type, and a staining pattern of the slide that is in a barcode or two-dimensional code type.

6. The method for identifying a target region of a digital pathology slide according to claim 5, wherein the method further comprising:

identifying the slide information region by using an OCR recognition method, to obtain an identification result; and naming, according to a preset rule, a file corresponding to the target region image based on the identification result.

7. The method for identifying a target region of a digital pathology slide according to claim 1, wherein the contour feature is at least one of a color feature, a shape feature, or a location feature of the scanned image of the pathology slide.

8. A system for identifying a target region of a digital pathology slide, wherein the system for identifying a target region of a digital pathology slide comprises:

an obtaining module, configured to obtain a scanned image of a pathology slide;

a processing module, configured to input the scanned image of the pathology slide into a preset deep learning-based identification model, wherein the preset deep learning-based identification model comprises an image contour feature extraction submodel, an image segmentation submodel, and an image classification submodel;

an extraction module, configured to extract a contour feature of the scanned image of the pathology slide by using the image contour feature extraction submodel, to obtain a contour image;

a segmentation module, configured to segment the contour image by using the image segmentation submodel to obtain a plurality of sub-contour images;

an identification module, configured to separately perform classification and identification on the plurality of sub-contour images by using the image classification submodel, to obtain a region category corresponding to each of the sub-contour images, wherein the region category comprises one of an effective pathological region, wherein the effective pathological region is defined as a region in which a diagnosis and analysis of a disease can be determined., a broken contaminant region, an experimental control region, and a slide information region; and a generation module, configured to determine a target region image based on the region category of each of the sub-contour images, wherein the target region image comprises an image in at least one region category of the effective pathological region, the broken contaminant region, the experimental control region, and the slide information region.

9. The system for identifying a target region of a digital pathology slide according to claim 8, wherein the obtaining module comprises:

a pattern determining unit, configured to select a to-be-scanned pathology slide, and determine a staining pattern based on slide information of the to-be-scanned pathology slide;

a parameter setting unit, configured to determine a target scanning parameter of a digital pathology slide scanner based on the staining pattern; and an image generation unit, configured to obtain the scanned image of the pathology slide that is generated by scanning the to-be-scanned pathology slide by the digital pathology slide scanner based on the target scanning parameter.

10. The system for identifying a target region of a digital pathology slide according to claim 8, wherein the system for identifying a target region of a digital pathology slide further comprisings:

an identification module, configured to identify the slide information region by using an OCR recognition method, to obtain an identification result; and a naming module, configured to name, according to a preset rule, a file corresponding to the target region image based on the identification result.

11. The system for identifying a target region of a digital pathology slide according to claim 8, wherein the generation module comprises:

a first determining subunit, configured to: if there are at least two effective pathological regions, select a region with highest definition from the at least two effective pathological regions as an optimal region, and determine an image of the optimal region as the target region image; and a second determining subunit, configured to: if there is one effective pathological region, combine a target region category to obtain the target region image.

12. The system for identifying a target region of a digital pathology slide according to claim 8, wherein the generation module is specifically configured to: receive a scanning instruction, and determine a target scanning mode of the to-be-scanned pathology slide according to the scanning instruction, where each target scanning mode corresponds to at least one of the region categories; determine a region category comprised in the target scanning mode as a target region category; and combine a target region category to obtain the target region image.

13. The system for identifying a target region of a digital pathology slide according to claim 8, wherein the slide information region is a combination of patient information and hospital information of the slide that are in a character type, and a staining pattern of the slide that is in a barcode or two-dimensional code type.

14. The system for identifying a target region of a digital pathology slide according to claim 8, wherein the contour feature is at least one of a color feature, a shape feature, or a location feature of the scanned image of the pathology slide.

15. A computer device, comprising a memory, a processor, and computer-readable instructions stored in the memory and capable of running on the processor, wherein when executing the computer-readable instructions, the processor implements the following steps:

obtaining a scanned image of a pathology slide;

inputting the scanned image of the pathology slide into a preset deep learning-based identification model, wherein the preset deep learning-based identification model comprises an image contour feature extraction submodel, an image segmentation submodel, and an image classification submodel;

extracting a contour feature of the scanned image of the pathology slide by using the image contour feature extraction submodel, to obtain a contour image;

segmenting the contour image by using the image segmentation submodel to obtain a plurality of sub-contour images;

separately performing classification and identification on the plurality of sub-contour images by using the image classification submodel, to obtain a region category corresponding to each of the sub-contour images, wherein the region category comprises one of an effective pathological region, wherein the effective pathological region is defined as a region in which a diagnosis and analysis of a disease can be determined, a broken contaminant region, an experimental control region, and a slide information region; and determining a target region image based on the region category of each of the sub-contour images, wherein the target region image comprises an image in at least one region category of the effective pathological region, the broken contaminant region, the experimental control region, and the slide information region.

16. The computer device according to claim 15, wherein the obtaining a scanned image of a pathology slide comprises:

selecting a to-be-scanned pathology slide, and determining a staining pattern based on slide information of the to-be-scanned pathology slide;

determining a target scanning parameter of a digital pathology slide scanner based on the staining pattern; and obtaining the scanned image of the pathology slide that is generated by scanning the to-be-scanned pathology slide by the digital pathology slide scanner based on the target scanning parameter.

17. The computer device according to claim 15, wherein the determining a the target region image based on the region category of each of the sub-contour images comprises:

receiving a scanning instruction, and determining a target scanning mode of the to-be-scanned pathology slide according to the scanning instruction, wherein each target scanning mode corresponds to at least one of the region categories;

determining a region category comprised in the target scanning mode as a target region category; and combining the target region category to obtain the target region image.

18. The computer device according to claim 17, wherein the combining the target region category to obtain the target region image comprises:

if there are at least two effective pathological regions, selecting a region with highest definition from the at least two effective pathological regions as an optimal region, and determining an image of the optimal region as the target region image; or if there is one effective pathological region, combining the target region category to obtain the target region image.

19. The computer device according to claim 15, wherein the slide information region is a combination of patient information and hospital information of the slide that are in a character type, and a staining pattern of the slide that is in a barcode or two-dimensional code type.

20. The computer device according to claim 19, wherein the steps further comprising;

identifying the slide information region by using an OCR recognition method, to obtain an identification result; and naming, according to a preset rule, a file corresponding to the target region image based on the identification result.

\*    \*    \*    \*    \*